United States Patent
Ohno et al.

(10) Patent No.: US 6,720,464 B2
(45) Date of Patent: Apr. 13, 2004

(54) PRODUCTION AND USE OF OCTAFLUOROPROPANE

(75) Inventors: Hiromoto Ohno, Kawasaki (JP); Toshio Ohi, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 95 days.

(21) Appl. No.: 10/111,773

(22) PCT Filed: Aug. 27, 2001

(86) PCT No.: PCT/JP01/07313

§ 371 (c)(1), (2), (4) Date: Apr. 29, 2002

(87) PCT Pub. No.: WO02/18305

PCT Pub. Date: Mar. 7, 2002

(65) Prior Publication Data

US 2003/0157800 A1 Aug. 21, 2003

Related U.S. Application Data

(60) Provisional application No. 60/241,838, filed on Oct. 20, 2000.

(30) Foreign Application Priority Data

Aug. 30, 2000 (JP) ........................................ 2000-260205

(51) Int. Cl.$^7$ .......................... C07C 17/00; C07C 17/08; C07C 19/08; C07C 21/18; C07C 21/20; C07C 21/22

(52) U.S. Cl. ........................ 570/169; 570/164; 570/165; 570/166; 570/167; 570/168; 570/175

(58) Field of Search ................................. 570/165, 164, 570/166, 167, 168, 169, 175

(56) References Cited

U.S. PATENT DOCUMENTS 4,158,023 A    6/1979  Von Halasz

FOREIGN PATENT DOCUMENTS

WO    WO 99/06342    2/1999

Primary Examiner—Johann Richter
Assistant Examiner—Elvis O. Price
(74) Attorney, Agent, or Firm—Sughrue Mion, PLLC

(57) ABSTRACT

Octafluoropropane is produced by a process comprising a step (1) of reacting hexafluoropropene with hydrogen fluoride in a gas phase at a temperature of from 150 to 450° C. in the presence of a fluorination catalyst to obtain 2H-heptafluoropropane and a step (2) of reacting 2H-heptafluoropropane obtained in step (1) with fluorine gas in a gas phase at a temperature of from 250 to 500° C. in the absence of a catalyst to obtain octafluoropropane. High-purity octafluoropropane is obtained which can be used in a process for producing a semiconductor device.

16 Claims, No Drawings

PRODUCTION AND USE OF OCTAFLUOROPROPANE

CROSS-REFERENCE TO RELATED APPLICATION

This application is an application filed under 35 U.S.C. §111 (a) claiming benefit pursuant to 35 U.S.C. §119 (e)(1) of the filing date of the Provisional Application No. 60/241,838 filed Oct. 20, 2000, pursuant to 35 §111 (b).

TECHNICAL FIELD

The present invention relates to a process for producing octafluoropropane, an octafluoropropane product, and uses thereof.

BACKGROUND ART

Octafluoropropane is used, for example, as a dry-etching or cleaning gas in the process for producing a semiconductor device. With respect to the production methods thereof, the following methods are known:

(1) a method of performing a direct fluorination reaction between hexafluoropropene and fluorine gas (see, Japanese Examined Patent Publication No. 62-61572 (JP-B-62-61572)), (2) a method of performing an electrolytic fluorination of hexafluoropropene in hydrogen fluoride (see, Japanese Examined Patent Publication No. 62-61115 (JP-B-62-61115)), (3) a method of reacting hexafluoropropene with fluorine in the presence of a catalyst (see, Japanese Examined Patent Publication No. 1-45455 (JP-B-1-45455)), and (4) a method of reacting hexafluoropropene with a high-order metal fluoride (see, Japanese Examined Patent Publication No. 62-54777 (JP-B-62-54777)).

However, in these methods, by-products such as tetrafluoromethane ($CF_4$) and hexafluoroethane ($C_2F_6$) are produced due to cleavage, $C_6F_{12}$ and $C_6F_{14}$ are produced due to radical addition, and a 4-membered ring is produced due to cyclization addition, for example, and as a result, the yield of and selectivity for the objective octafluoropropane decrease. Furthermore, some compounds in these impurities are difficult to separate by distillation and, in turn, high-purity octafluoropropane can hardly be obtained. Particularly, in the case of using hexafluoropropene as the starting material, chloropentafluoroethane (CFC-115) contained as an impurity scarcely reacts with fluorine gas and mostly remains in the objective octafluoropropane and since this impurity compound can hardly be separated by distillation, due to the similar boiling points, production of high-purity octafluoropropane is difficult.

DISCLOSURE OF INVENTION

The present invention has been made under these circumstances and the object of the present invention is to provide a method for producing octafluoropropane of high purity which can be used in a process of producing a semiconductor device, to provide high-purity octafluoropropane and to the uses thereof.

As a result of extensive investigations to attain the above-described object, the present inventors have found that high-purity octafluoropropane can be produced by using a production process comprising (1) a step of reacting hexafluoropropene with hydrogen fluoride in a gas phase at a temperature of 150 to 450° C. in the presence of a fluorination catalyst to obtain 2H-heptafluoropropane and (2) a step of reacting 2H-heptafluoropropane obtained in the step (1) with fluorine gas in a gas phase at a temperature of 250 to 500° C. in the absence of a catalyst to obtain octafluoropropane. The present invention has been accomplished based on this finding.

More specifically, the present invention (I) is a process for producing octafluoropropane, comprising (1) a step of reacting hexafluoropropene with hydrogen fluoride in a gas phase at a temperature of 150 to 450° C. in the presence of a fluorination catalyst to obtain 2H-heptafluoropropane and (2) a step of reacting 2H-heptafluoropropane obtained in the step (1) with fluorine gas in a gas phase at a temperature of from 250 to 500° C. in the absence of a catalyst to obtain octafluoropropane. In a preferred embodiment of the present invention (I), the starting hexafluoropropene contains at least one compound selected from the group consisting of dichlorodifluoromethane, chlorodifluoromethane, chloropentafluoroethane, chlorotetrafluoroethane and chlorotrifluoroethylene; and in the step (1), the fluorination catalyst is a bulk catalyst mainly comprising an oxide of chromium and obtained by adding at least one member selected from the group consisting of indium, zinc and nickel, and the molar ratio of hydrogen fluoride/hexafluoropropene is in the range from 0.8 to 3:1.

In a preferred embodiment of the present invention (I), a step of removing impurities contained in 2H-heptafluoropropane is provided before the step (2); the impurities are at least one compound selected from the group consisting of tetrafluoromethane, trifluoromethane, chlorotrifluoromethane, hexafluoroethane and pentafluoroethane; the step of removing impurities is a distillation step; and the 2H-heptafluoropropane has a chlorine compound content of 0.01 vol % or less.

In a preferred embodiment of the present invention (I), the step (2) is performed in the presence of a diluting gas and the diluting gas is at least one gas selected from the group consisting of hydrogen fluoride, tetrafluoromethane, hexafluoroethane and octafluoropropane; and in the step (2), the molar ratio of fluorine gas/2H-heptafluoropropane is in the range from 0.9 to 1.5:1, and the 2H-heptafluoropropane concentration at the reactor inlet is 8 mol % or less.

In a preferred embodiment of the present invention (I), at least a part of the outlet gas of the step (2) is circulated and reused as a diluting gas in the step (2); a step of reacting at least a part of the outlet gas of the step (2) with at least one hydrofluorocarbon to remove unreacted fluorine gas contained in the outlet gas is provided; the hydrofluorocarbon is selected from the group consisting of trifluoromethane, tetrafluoroethane, pentafluoroethane and 2H-heptafluoropropane; hydrogen fluoride contained in the outlet gas of the step (2) is separated and the separated hydrogen fluoride is returned to the step (1) and/or the step (2); and at least a part of the octafluoropropane is separated from the gas after the separation of hydrogen fluoride, and the remaining gas is returned to the step (1) and/or the step (2).

The present invention (II) is an octafluoropropane product comprising octafluoropropane having a purity of 99.995 vol % or more. In a preferred embodiment, the total amount of compounds having a chlorine atom within the molecule and cyclic compounds is 50 volppm or less based on the octafluoropropane product.

The present invention (III) is an etching gas comprising the above-described octafluoropropane product. The present invention (IV) is a cleaning gas comprising the above-described octafluoropropane product.

BEST MODE FOR CARRYING OUT THE INVENTION

The present invention is described in detail below.

The hexafluoropropene ($CF_3CF=CF_2$) for use in the present invention (I) may be obtained as a by-product, for example, in the process of producing tetrafluoroethylene ($CF_2=CF_2$) through thermal decomposition of chlorodifluoromethane ($CHClF_2$), or obtained, as described in Japanese Unexamined Patent Publication No. 4-145033 (JP-A-4-145033), by a method of chlorofluorinating, optionally with dehalogenation, propane, propylene or a partially halogenated C3 acyclic hydrocarbon. However, in the hexafluoropropene obtained by these methods, compounds having a chlorine atom within the molecule are intermixed as impurities in many cases, such as dichlorodifluoromethane, chlorodifluoromethane, chloropentafluoroethane, chlorotetrafluoroethane and chlorotrifluoroethylene. The present invention provides a process of producing octafluoropropane starting from hexafluoropropene which may contain such impurities. Here, the boiling points of the intermediate 2H-heptafluoropropane, the objective octafluoropropane and the above-described impurities are shown in Table 1 below.

TABLE 1

| Name of Compound | Structural Formula | Boiling Point |
|---|---|---|
| Chlorodifluoromethane | $CHClF_2$ | −41° C. |
| Chloropentafluoroethane | $CF_3CClF_2$ | −39.3° C. |
| Octafluoropropane | $CF_3CF_2CF_3$ | −36.7° C. |
| Dichlorodifluoromethane | $CCl_2F_2$ | −29.2° C. |
| Hexafluoropropene | $CF_3CF=CF_2$ | −29° C. |
| Chlorotrifluoroethylene | $CF_2=CClF$ | −27.9° C. |
| 2H-Heptafluoropropane | $CF_3CHFCF_3$ | −15.2° C. |
| Chlorotetrafluoroethane | $CF_3CHClF$ | −12° C. |

As is apparent from the boiling points shown in Table 1, the boiling points of the compounds having a chlorine atom within the molecule, which are contained in the starting hexafluoropropene, are approximated to the boiling point of the resulting octafluoropropane, therefore, these compounds can hardly be separated by only a distillation operation.

In the process for producing octafluoropropane of the present invention (I), a step (1) of reacting hexafluoropropene with hydrogen fluoride in a gas phase at a temperature of from 150 to 450° C. in the presence of a fluorination catalyst to obtain 2H-heptafluoropropane is first performed. Step (1) has the following two advantageous points.

[1] In the case of directly fluorinating hexafluoropropene with fluorine gas or performing the direct fluorination reaction with fluorine gas in the presence of a catalyst or high-order metal fluoride, various by-products are produced due to a cleavage reaction of carbon-carbon bond, a radical addition reaction, a cyclization reaction or the like. Accordingly, not only the yield and selectivity are reduced but also high-purity octafluoropropane can hardly be obtained. In the present invention, hydrogen fluoride is added to hexafluoropropene to obtain the intermediate 2H-heptafluoropropane in a high yield with high selectivity, whereby the production of by-products due to those reactions can be suppressed.

[2] As described above, hexafluoropropene contains compounds having chlorine atom within the molecule as impurities in many cases and these compounds are difficult to remove by a distillation operation. In the present invention, at the same time as the reaction of adding hydrogen fluoride to hexafluoropropene to obtain 2H-heptafluoropropane as an intermediate, compounds having a chlorine atom within the molecule are fluorinated using the hydrogen fluoride and thereby converted into compounds which are easy to separate by distillation.

The reaction of adding hydrogen fluoride to hexafluoropropene proceeds according to the following formula (1) in the presence of a fluorination catalyst:

$$CF_3CF=CF_2+HF \rightarrow CF_3CHFCF_3 \qquad (1)$$

The fluorination catalyst may be a commonly used chromium-based catalyst. In the case where hexafluoropropene contains chlorine-containing impurities and the chlorine-containing impurities are fluorinated and thereby converted into other compounds, the reaction temperature becomes higher, therefore, a bulk catalyst mainly comprising an oxide of chromium and obtained by adding at least one member selected from indium, zinc and nickel is preferably used, because this catalyst has excellent activity (performance) and high stability (catalyst life). A supported catalyst (e.g. on an alumina support) may also be used, however, a bulk catalyst is preferred in view of activity and stability. Such a catalyst may be activated by a fluorination treatment with hydrogen fluoride before use in the reaction.

In the step (1), the reaction temperature varies depending on the kind or content of impurities in hexafluoropropene but it is in the range from 150 to 450° C., preferably from 200 to 350° C. In the case where CFC-115 is contained as an impurity in hexafluoropropene, the reaction temperature is suitably in the range from 350 to 450° C., preferably from 350 to 400° C. If the reaction temperature exceeds 450° C., the catalyst is disadvantageously liable to decrease in stability, whereas if it is less than 150° C., the conversion in the objective reaction is reduced or the fluorination reaction of impurity compounds slowly proceeds, and these effects are not preferred.

The molar ratio (HF/FC-1216) between hydrogen fluoride and hexafluoropropene (FC-1216) is preferably from 0.8 to 3.0:1, more preferably from 1.0 to 2.0:1. If the molar ratio between hydrogen fluoride and hexafluoropropene is less than 0.8:1, the conversion of hexafluoropropylene may fall, whereas if the molar ratio exceeds 3.0:1, the cost for equipment for recovering unreacted HF increases and this is not preferred.

As described above, the starting hexafluoropropene may contain, as impurities, compounds having a chlorine atom within the molecule and these impurities are usually difficult to separate by distillation. Examples of the compounds having a chlorine atom within the molecule include chlorodifluoromethane, chloropentafluoroethane, dichlorodifluoromethane, chlorotrifluoroethylene and chlorotetrafluoroethane. In the present invention (I), these compounds having chlorine are converted into other fluorocompounds which are easy to separate by distillation, during the main reaction in the step of reacting hexafluoropropene with hydrogen fluoride in the presence of a fluorination catalyst to obtain 2H-heptafluoropropane.

The chlorine compounds can be converted into other fluorine compounds, for example, by the following reactions (2) to (5):

$$CHClF_2+HF \rightarrow CHF_3+HCl \qquad (2)$$

$$CF_2=CClF+HF \rightarrow CF_3CHClF \qquad (3)$$

$$CF_3CHClF+HF \rightarrow CF_3CHF_2+HCl \qquad (4)$$

$$CF_3CClF_2+HF \rightarrow CF_3CF_3+HCl \qquad (5)$$

The boiling points of these fluorinated compounds and 2H-heptafluoropropane as an intermediate are shown in Table 2.

TABLE 2

| Name of Compound | Structural Formula | Boiling Point |
| --- | --- | --- |
| Tetrafluoromethane | $CF_4$ | −128° C. |
| Trifluoromethane | $CHF_3$ | −84.4° C. |
| Chlorotrifluoromethane | $CClF_3$ | −81.4° C. |
| Hexafluoroethane | $CF_3CF_3$ | −78.1° C. |
| Pentafluoroethane | $CF_3CHF_2$ | −48.5° C. |
| 2H-Heptafluoropropane | $CF_3CHFCF_3$ | −15.2° C. |

As is apparent from Table 2, there is obviously a large difference in boiling point between 2H-heptafluoropropane as an intermediate and the compounds fluorinated according to the above-described reactions, as a result, separation of these compounds by distillation is facilitated.

The gas mainly comprising 2H-heptafluoropropane obtained in the step (1) is then introduced into a dehydrohalogenation step of separating hydrogen chloride and unreacted hydrogen fluoride therefrom. The hydrogen chloride and hydrogen fluoride are further separated from each other by distillation and thereafter, the hydrogen chloride is neutralized with an aqueous alkali solution. The hydrogen fluoride may be returned to the step of fluorinating hexafluoropropene or may be neutralized with an aqueous alkali solution. After the separation of hydrogen chloride and hydrogen fluoride in the dehydrohalogenation step, the gas mainly comprising 2H-heptafluoropropane is subjected to a treatment in the step (2) but before that, the gas is preferably introduced into a distillation tower to remove impurities contained in the 2H-heptafluoropropane.

Examples of the impurities contained in 2H-heptafluoropropane include tetrafluoromethane, trifluoromethane, chlorotrifluoromethane, hexafluoroethane and pentafluoroethane. These impurities are preferably removed by distillation. In the distillation tower, tetrafluoromethane, trifluoromethane, chlorotrifluoromethane, hexafluoroethane and pentafluoroethane as low boiling fractions are extracted from the top of the distillation tower, and 2H-heptafluoropropane is extracted from the bottom. This gas mainly comprising 2H-heptafluoropropane is used as a starting material in the direct fluorination reaction with fluorine gas. Irrespective of the presence or absence of distillation after the dehydrohalogenation step, the content of chlorine compounds contained as impurities in 2H-heptafluoropropane is preferably 0.01 vol % or less, more preferably 0.005 vol % or less.

The step (2) is described below.

The step (2) is a direct fluorination reaction step of reacting 2H-heptafluoropropane obtained in the fluorination step of the step (1) with fluorine gas in the gas phase at a temperature of from 250 to 500° C. in the absence of a catalyst to obtain octafluoropropane. This step has the following three advantageous points.

[1] In the case of reacting hydrofluorocarbon with fluorine gas to produce perfluorocarbon, a huge heat of reaction is generated. The heat of reaction is proportional to the molar number of fluorine reacted per one molecule. As the amount of fluorine becomes larger, the heat of reaction becomes larger, the possibility of cleavage of a carbon-carbon bond, polymerization, cyclization addition or, depending on the case, explosion is higher, and the yield is lower, and this gives rise to problems in industrial production or operation. In order to prevent abrupt generation of the heat of reaction in the direct fluorination reaction, a method of diluting fluorine with an inert gas (e.g., nitrogen or helium) and a method of diluting an organic material as the substrate are known. An inert gas such as nitrogen and helium is not advantageous, in view of the cost, considering the separation and purification from the objective perfluorocarbon in the distillation step. In the present invention (I), at least one gas selected from the group consisting of hydrogen fluoride, tetrafluoromethane, hexafluoroethane and octafluoropropane is used as the diluting gas, whereby the above-described problems can be solved.

[2] In the present invention (I), the reaction may be performed by setting the concentration of the reaction substrate 2H-heptafluoropropane at the reactor inlet to be lower than the explosion range using a diluting gas, specifically, to 8 mol % or less. As described above, in the direct fluorination reaction using fluorine gas, the fluorine gas used is extremely abundant in the reactivity, therefore, when the organic compound as a substrate (particularly a compound containing hydrogen) is exposed to the fluorine gas, combustion or explosion may take place and this is dangerous. In the step (2), since 2H-heptafluoropropane used as the substrate contains a hydrogen atom, the matter of importance is to prevent explosion between 2H-heptafluoropropane and fluorine gas. In order to prevent the explosion, the mixed gas composition must be out of the explosion range. The present inventors have studied on the explosion range between 2H-heptafluoropropane and fluorine gas and, as a result, the lower limit in the explosion range of 2H-heptafluoropropane was found to be 8 mol % or less. Thus, the 2H-heptafluoropropane concentration at the reaction inlet can be set within the safety range.

[3] In the direct fluorination reaction of reacting 2H-heptafluoropropane with fluorine gas, if 2H-heptafluoropropane is used in excess based on the fluorine gas, a step of removing fluorine gas may be dispensed with but great difficulties are incurred in the later separation and purification. In the step (2) of the present invention (I), the fluorine gas can be used in an excess molar amount based on 2H-heptafluoropropane so as to elevate the reaction efficiency and when fluorine gas is used in excess, the reaction production gas outflowing from the reaction step contains the excess fluorine gas in addition to perfluorocarbon and hydrogen fluoride. For treating the excess fluorine gas, a method of reacting the gas with an inorganic oxide such as alumina or soda lime is known, however, this method is not preferred because water is produced by the reaction and causes corrosion of apparatus materials. In the present invention (I), the excess fluorine gas can be removed by contacting the gas with hydrofluorocarbon at 1.1 molar times, in terms of the chemical equivalent ratio, to the excess fluorine gas.

The direct fluorination reaction of reacting 2H-heptafluoropropane with fluorine gas proceeds according to the following formula (6):

$$CF_3CHFCF_3 + F_2 \rightarrow CF_3CF_2CF_3 + HF \quad (6)$$

This reaction may be performed using a catalyst but may also be performed in the absence of a catalyst. Furthermore, as described above, the direct fluorination reaction of reacting hydrofluorocarbon with fluorine gas is accompanied with generation of much heat of reaction, therefore, this reaction is preferably performed in the presence of a diluting gas. The diluting gas for use in this reaction may be at least one gas selected from the group consisting of hydrogen fluoride, tetrafluoromethane, hexafluoroethane and octafluoropropane. Among these, preferred are hydrogen fluoride and/or octafluoropropane, more preferred is a gas abundant in hydrogen fluoride.

For introducing the diluting gas, a method of diluting either one or both of 2H-heptafluoropropane and fluorine gas with a diluting gas and then introducing these into a reactor may be used. The concentration of the substrate 2H-heptafluoropropane at the reactor inlet is preferably set to 8 mol % or less which is lower than the explosion range, more preferably 6 mol % or less. The concentration of fluorine gas at the reactor inlet is preferably set such that the molar ratio of fluorine gas/2H-heptafluoropropane becomes from 0.9 to 1.5:1, more preferably from 0.9 to 1.2:1. If the fluorine concentration is set to give a molar ratio of fluorine gas/2H-heptafluoropropane of less than 0.9:1, the conversion of 2H-heptafluoropropane may decrease, whereas if set to give a molar ratio in excess of 1.5:1, the step for removing unreacted fluorine may disadvantageously bear a burden. Furthermore, if the molar ratio of fluorine gas/2H-heptafluoropropane exceeds 1.5:1, when the outlet gas of the step (2) is circulated and reused as the diluting gas of the step (2), the fluorine concentration in the circulating gas (diluting gas) may increase and there may arise a problem such as an explosion.

The 2H-heptafluoropropane and fluorine gas diluted with a diluting gas to a concentration lower than the explosion range can be reacted in a gas phase. The reaction temperature is suitably from 250 to 500° C., preferably from 350 to 450° C. If the reaction temperature is less than 250° C., the reaction proceeds slowly, whereas if it exceeds 500° C., the carbon-carbon bond in the objective octafluoropropane is liable to cleave and this is not preferred.

The outlet gas of the step (2) mainly comprises hydrogen fluoride and octafluoropropane. In the present invention (I), at least a part of the outlet gas can be circulated and reused as a diluting gas in the step (2). In some cases, the outlet gas contains unreacted fluorine gas and if this is the case, for detecting the concentration of unreacted fluorine gas, a method of continuously introducing a very slight amount of outlet gas into the continuously flowing solution containing a metal iodide to produce iodine, measuring the transmittance of visible light in a specific wavelength region through the solution, thereby continuously quantitating the iodine produced, and calculating the concentration of unreacted fluorine, may be used. For detecting fluorine compounds and determining the reaction rate, a method of measuring the concentrations of perfluorocarbon, hydrofluorocarbon and hydrogen fluoride contained in the mixed gas according to an infrared spectrometry may be used. By this determining, the operation can be continuously performed, industrially, under safe conditions.

In addition to the reuse of outlet gas of the step (2) as the diluting gas by circulation, when unreacted fluorine gas is contained therein, the reaction outlet gas is preferably extracted in almost the same amount, for example, as 2H-heptafluoropropane fed, introduced into the step of removing unreacted fluorine and then contacted with hydrofluorocarbon in 1.1 molar times in terms of the chemical equivalent ratio to excess fluorine gas, to remove fluorine gas. The contacting temperature in the step of removing fluorine gas varies depending on the kind of hydrofluorocarbon but it is preferably from 250 to 500° C., more preferably from 350 to 450° C. The concentration of fluorine in the outlet gas after the fluorine-removing step may usually be 50 ppm or less and depending on the condition, may be 10 ppm or less. Examples of the hydrofluorocarbon which can be used for the reaction with excess fluorine gas include trifluoromethane, tetrafluoroethane, pentafluoroethane and 2H-heptafluoropropane.

The outlet gas of step (2), exclusive of the part of the outlet gas circulated and reused as the diluting gas in the step (2), is, when fluorine gas remains therein, introduced into a partial condensation step after passing through the fluorine-removing step. The main components of the outlet gas are hydrogen fluoride and octafluoropropane and in the partial condensation step, the system is cooled to cause liquid separation of hydrogen fluoride, and octafluoropropane is mainly separated as a gas. The hydrogen fluoride separated can be circulated and reused by returning it to the fluorination step (1) and/or the direct fluorination step (2). The gas mainly comprising octafluoropropane, which is separated as a gas, is passed through a dehydration step, pressurized by a compressor and introduced into a distillation tower.

After the gas mainly comprising octafluoropropane is introduced into a distillation tower, low boiling fractions are extracted from the top of, for example, a first distillation tower. The low boiling fractions are inert gas, tetrafluoromethane, hexafluoroethane and the like, and can be used as the diluting gas in the direct fluorination step (2). The gas mainly comprising octafluoropropane extracted from the bottom is introduced into a second distillation tower and in the second distillation tower, octafluoropropane is extracted as a low boiling fraction from the top and then introduced into a product step. The high boiling fraction extracted from the bottom in the second distillation tower may be returned to the step (2) and used as the diluting gas or, depending on the case, may be decomposed using a harmful-gas removing agent or the like.

The objective octafluoropropane introduced into the product step is further purified, if desired, and introduced into a product tank, depending on the case, through a dehydration step. The purity of the octafluoropropane introduced into the product tank can be determined by an analysis method such as (1) gas chromatography (GC) using TCD, FID or ECD, or (2) gas chromatography-mass spectrometer (GC-MS). The present invention (II) is a high-purity octafluoropropane having a purity of 99.995 vol % or more, which is obtained using the production process of the present invention (I). With respect to the impurities contained in the octafluoropropane, the total amount of compounds having chlorine atom within the molecule and cyclic compounds is 50 volppm or less and the total amount of these impurities can also be reduced to 10 volppm or less.

The present invention (III) and the present invention (IV), which are uses of the high-purity octafluoropropane obtained using the production process of the present invention (I), are described below.

The high-purity octafluoropropane of the present invention (II) can be used as an etching gas in an etching step in a process of producing a semiconductor device and can also be used as a cleaning gas in a cleaning step in a process of producing a semiconductor device. In the production process of a semiconductor device such as an LSI or a TFT, a thin or thick film is formed using a CVD method, a sputtering method or a vapor deposition method, and the film is etched to form a circuit pattern. In the apparatus for forming the thin or thick film, cleaning is performed to remove unnecessary deposits accumulated on the inner wall of the apparatus, jig, pipeline and the like, because unnecessary deposits cause generation of particles and must be removed, occasionally, to produce a good-quality film. In the use as an etching or cleaning gas, the octafluoropropane of the present invention may be diluted with an inert gas such as He, Ar and $N_2$, or may be used by mixing it with a gas such as $F_2$, $NF_3$, $C_2F_4$, HCl, $O_2$ and $H_2$, at an appropriate ratio.

The present invention is described in greater detail below by referring to the Examples and Comparative Examples, however, the present invention should not be construed as being limited to these Examples.

STARTING MATERIAL EXAMPLE 1

A starting material hexafluoropropene having the composition shown in Table 3 was obtained after a separation and distillation operation of HFP (hexafluoropropene) obtained as a by-product in the process of thermally decomposing HCFC-22 ($CHClF_2$) together with water vapor on alumina to produce TFE (tetrafluoroethylene).

TABLE 3

| Name of Compound | Chemical Formula | Composition (vol %) |
|---|---|---|
| Hexafluoropropene | $CF_3CF=CF_2$ | 99.9685 |
| Tetrafluoroethylene | $CF_2=CF_2$ | 0.0033 |
| Chlorotrifluoroethylene | $CF_2=CClF$ | 0.0008 |
| Dichlorotetrafluoroethane | $CF_3CCl_2F$ | 0.0011 |
| Chloropentafluoroethane | $CF_3CClF_2$ | 0.0192 |
| Pentafluoroethane | $CF_3CHF_2$ | 0.0028 |
| Chlorotrifluoroethane | $CF_3CH_2Cl$ | 0.0004 |
| Chlorodifluoromethane | $CHClF_2$ | 0.0039 |

STARTING MATERIAL EXAMPLE 2

A commercially available hexafluoropropene was analyzed and found to have the composition shown in Table 4.

TABLE 4

| Name of Compound | Chemical Formula | Composition (vol %) |
|---|---|---|
| Hexafluoropropene | $CF_3CF=CF_2$ | 99.9196 |
| Tetrafluoroethylene | $CF_2=CF_2$ | 0.0008 |
| Chlorotrifluoroethylene | $CF_2=CClF$ | 0.0004 |
| Chloropentafluoroethane | $CF_3CClF_2$ | 0.0414 |
| Dichlorodifluoromethane | $CCl_2F_2$ | 0.0248 |
| Chlorodifluoromethane | $CHClF_2$ | 0.0069 |
| Chlorodifluoroethylene | $CF_2=CHCl$ | 0.0042 |
| Tetrafluoroethane | $CF_3CH_2F$ | 0.0019 |

Production of Fluorination Catalyst

Into a 10 L container containing 0.6 L of purified water, a solution obtained by dissolving 452 g of $Cr(NO_3)_3 \cdot 9H_2O$ and 42 g of $In(NO_3)_3 \cdot nH_2O$ (n is about 5) in 1.2 L of purified water, and 0.31 L of 28% aqueous ammonia were added dropwise over about 1 hour while stirring under the control of respective flow rates of two aqueous solutions to give a reaction solution having a pH of 7.5 to 8.5. The resulting hydroxide slurry was filtered, thoroughly washed with purified water and then dried at 120° C. for 12 hours. The thus-obtained solid was pulverized, mixed with graphite and then pelletized by a tabletting machine. The pellets obtained were calcined at 400° C. for 4 hours in a nitrogen stream to obtain a catalyst precursor. Into an Inconel-made reactor, the catalyst precursor was filled and subsequently subjected to a fluorination treatment (activation of catalyst) at an atmospheric pressure and 350° C. in a stream of HF diluted with nitrogen and then in a 100% HF stream to prepare a catalyst.

EXAMPLE 1

Into an Inconel 600-type reactor having an inner diameter of 1 inch and a length of 1 m, 100 ml of the catalyst, prepared according to the method described in the above Production of Fluorination Catalyst, was filled, and the temperature was elevated to 400° C. while passing nitrogen therethrough. Thereto, hydrogen fluoride was fed at 6.32 NL/hr and then the gas mainly comprising hexafluoropene as described in Starting Material Example 1 was fed at 3.24 NL/hr. By stopping the feeding of nitrogen gas, the reaction was initiated. After 2 hours, the discharged gas was washed with an aqueous potassium hydroxide solution to remove the acid content and thereafter, the gas composition was analyzed by gas chromatography and, as a result, a gas having the composition shown in Table 5 was obtained.

TABLE 5

| Name of Compound | Chemical Formula | Composition (vol %) |
|---|---|---|
| 2H-Heptafluoropropane | $CF_3CHFCF_3$ | 99.9611 |
| Trifluoromethane | $CHF_3$ | 0.0053 |
| Hexafluoroethane | $CF_3CF_3$ | 0.0192 |
| Pentafluoroethane | $CF_3CHF_2$ | 0.0071 |
| Octafluoropropane | $CF_3CF_2CF_3$ | 0.0004 |
| Hexafluoropropene | $CF_3CF=CF_2$ | 0.0052 |
| Chloropentafluoroethane | $CF_3CClF_2$ | 0.0008 |
| Tetrafluoroethane | $CF_3CH_2F$ | 0.0008 |
| Chlorotrifluoroethane | $CF_3CH_2Cl$ | 0.0001 |

The gas after the removal of acid content was collected under cooling using a cylinder container and distillation-purified to remove low boiling fractions and high boiling fractions by a known method. The composition obtained after the distillation and purification was analyzed by gas chromatography and found to have the composition shown in Table 6.

TABLE 6

| Name of Compound | Chemical Formula | Composition (vol %) |
|---|---|---|
| 2H-Heptafluoropropane | $CF_3CHFCF_3$ | 99.9965 |
| Pentafluoroethane | $CF_3CHF_2$ | 0.0003 |
| Octafluoropropane | $CF_3CF_2CF_3$ | 0.0001 |
| Hexafluoropropene | $CF_3CF=CF_2$ | 0.0019 |
| Chloropentafluoroethane | $CF_3CClF_2$ | 0.0007 |
| Tetrafluoroethane | $CF_3CH_2F$ | 0.0005 |

From the results shown in Table 6, it was found that chlorine compounds contained as impurities in 2H-heptafluoropropane can be reduced to 0.01 vol % or less by distillation.

EXAMPLE 2

Using the gas mainly comprising 2H-heptafluoropropane after the distillation obtained in Example 1, a direct fluorination reaction with fluorine gas was performed.

A nickel reactor having an inner diameter of 20.6 mm$\phi$ and a length of 500 mm (using heating by an electric heater; the reactor had been subjected to a passivation treatment with fluorine gas at a temperature of 500° C.) was heated to a temperature of 400° C. while passing nitrogen gas at 20 NL/hr.

Then, hydrogen fluoride (diluting gas) was fed at 60 NL/hr through two branches and, into one gas flow, the gas mainly comprising 2H-heptafluoropropane was fed at 3.24 NL/hr. Thereafter, fluorine gas was fed into another gas flow of hydrogen fluoride at 3.55 NL/hr, the feeding of nitrogen gas was stopped, and the direct fluorination reaction was performed. After 3 hours, the reaction product gas was washed with an aqueous potassium hydroxide solution and an aqueous potassium iodide solution, analyzed on hydrogen fluoride and unreacted fluorine gas, and after removing the acid content, analyzed by gas chromatography. As a result, the organic material was found to have the gas composition shown in Table 7.

TABLE 7

| Name of Compound | Chemical Formula | Composition (vol %) |
|---|---|---|
| Octafluoropropane | $CF_3CF_2CF_3$ | 99.1042 |
| Tetrafluoromethane | $CF_4$ | 0.0011 |
| Hexafluoroethane | $CF_3CF_3$ | 0.0017 |
| 2H-Heptafluoropropane | $CF_3CHFCF_3$ | 0.8762 |
| Chloropentafluoroethane | $CF_3CClF_2$ | 0.0006 |
| Perfluorohexane | $C_6F_{14}$ | 0.0162 |

The amount of unreacted fluorine gas in the reaction outlet gas was 0.26 NL/hr.

The gas after the removal of acid content was collected under cooling using a cylinder container and distillation-purified to remove low boiling fractions and high boiling fractions by a known method. The composition obtained after the distillation and purification was analyzed by gas chromatography and found to have the composition shown in Table 8.

TABLE 8

| Name of Compound | Chemical Formula | Composition (vol %) |
|---|---|---|
| Octafluoropropane | $CF_3CF_2CF_3$ | 99.9992 |
| 2H-Heptafluoropropane | $CF_3CHFCF_3$ | 0.0002 |
| Chloropentafluoroethane | $CF_3CClF_2$ | 0.0006 |

From the results shown in Table 8, octafluoropropane obtained was found to have a purity of 99.999 vol % or more.

EXAMPLE 3

Into a nickel reactor having an inner diameter of 20.6 mmφ and a length of 500 mm, the outlet gas containing unreacted fluorine gas obtained after the direct fluorination reaction in Example 2 was introduced. The gas composition was such that the hydrogen fluoride flow was 62.82 NL/hr, the organic material flow was 3.16 NL/hr and the unreacted fluorine gas flow was about 0.26 NL/hr. The reactor temperature was elevated to 390° C., trifluoromethane as hydrofluorocarbon was fed at about 0.286 NL/hr from the reactor inlet, and unreacted fluorine and organic material composition were analyzed by titration and gas chromatography. The amount of unreacted fluorine gas in the outlet gas after the reaction with trifluoromethane was 50 ppm or less, and the outlet gas had the composition shown in Table 9.

TABLE 9

| Name of Compound | Chemical Formula | Composition (vol %) |
|---|---|---|
| Octafluoropropane | $CF_3CF_2CF_3$ | 91.6849 |
| Tetrafluoromethane | $CF_4$ | 5.2707 |
| Trifluoromethane | $CHF_3$ | 3.0232 |
| Hexafluoroethane | $CF_3CF_3$ | 0.0028 |
| 2H-Heptafluoropropane | $CF_3CHFCF_3$ | 0.0029 |
| Chloropentafluoroethane | $CF_3CClF_2$ | 0.0006 |
| Perfluorohexane | $C_6F_{14}$ | 0.0149 |

Subsequently, the outlet gas after the removal of remaining fluorine gas was washed with an aqueous potassium hydroxide solution to remove hydrogen fluoride. The gas after the removal of acid content was collected under cooling using a cylinder container and purified by distillation to remove low boiling fractions and high boiling fractions by a known method. The gas obtained after the purification was analyzed by gas chromatography and found to have the composition shown in Table 10.

TABLE 10

| Name of Compound | Chemical Formula | Composition (vol %) |
|---|---|---|
| Octafluoropropane | $CF_3CF_2CF_3$ | 99.9993 |
| 2H-Heptafluoropropane | $CF_3CHFCF_3$ | 0.0001 |
| Chloropentafluoroethane | $CF_3CClF_2$ | 0.0006 |

COMPARATIVE EXAMPLE 1

A direct fluorination reaction of reacting hexafluoropropene with fluorine gas was performed. A nickel reactor having an inner diameter of 20.6 mmφ and a length of 500 mm (using heating by an electric heater; the reactor had been subjected to a passivation treatment with fluorine gas at a temperature of 500° C.) was heated to a temperature of 50° C. while passing nitrogen gas at 60 NL/hr through two branches. Into one nitrogen gas flow, the gas mainly comprising hexafluoropropane described in Starting Material Example 1 was fed at 3.24 NL/hr. Subsequently, fluorine gas was fed into another nitrogen gas flow at 3.55 NL/hr and the direct fluorination reaction was performed. After 2 hours, the reaction product gas was washed with an aqueous potassium hydroxide solution and an aqueous potassium iodide solution to remove unreacted fluorine gas, and analyzed by gas chromatography. As a result, the gas had the composition shown in Table 11.

TABLE 11

| Name of Compound | Chemical Formula | Composition (vol %) |
|---|---|---|
| Octafluoropropane | $CF_3CF_2CF_3$ | 93.3515 |
| Hexafluoroethane | $CF_3CF_3$ | 0.0063 |
| Chlorotrifluoromethane | $CClF_3$ | 0.0039 |
| Chloropentafluoroethane | $CF_3CClF_2$ | 0.0204 |
| Dichlorotetrafluoroethane | $CF_3CCl_2F$ | 0.0011 |
| Perfluorohexane | $C_6F_{14}$ | 6.6122 |
| Octafluorocyclobutane | $C_4F_8$ | 0.0046 |

As is proved from the results shown in Table 11, the method of producing octafluoropropane by a direct fluorination reaction between hexafluoropropene and fluorine gas was found to cause generation of polymerization, cyclization addition or the like, and decrease in the yield.

Then, the gas after the removal of acid content was collected under cooling using a cylinder container and distillation-purified to remove low boiling fractions and high boiling fractions by a known method. The composition obtained after the distillation and purification was analyzed by gas chromatography and found to have the composition shown in Table 12.

TABLE 12

| Name of Compound | Chemical Formula | Composition (vol %) |
|---|---|---|
| Octafluoropropane | $CF_3CF_2CF_3$ | 99.9768 |
| Chloropentafluoroethane | $CF_3CClF_2$ | 0.0218 |
| Octafluorocyclobutane | $C_4F_8$ | 0.0022 |

As is proved from the results shown in Table 12, it is difficult to separate octafluoropropane, chloropentafluoroethane as chlorine compound, and octafluorocyclobutane as cyclic compound, and thereby attain purification to a high purity.

EXAMPLE 4

A reaction was performed by the same operations and under the same conditions as in Example 1 except for changing the starting material hexafluoropropene to Starting Material Example 2. The gas after the removal of acid content was analyzed and found to have the composition shown in Table 13.

TABLE 13

| Name of Compound | Chemical Formula | Composition (vol %) |
|---|---|---|
| 2H-Heptafluoropropane | $CF_3CHFCF_3$ | 99.9079 |
| Trifluoromethane | $CHF_3$ | 0.0098 |
| Hexafluoroethane | $CF_3CF_3$ | 0.0414 |
| Pentafluoroethane | $CF_3CHF_2$ | 0.0028 |
| Chlorotrifluoromethane | $CClF_3$ | 0.0236 |
| Octafluoropropane | $CF_3CF_2CF_3$ | 0.0005 |
| Hexafluoropropene | $CF_3CF=CF_2$ | 0.0049 |
| Chloropentafluoroethane | $CF_3CClF_2$ | 0.0004 |
| Tetrafluoroethane | $CF_3CH_2F$ | 0.0029 |
| Dichlorodifluoromethane | $CCl_2F_2$ | 0.0012 |
| Chlorotetrafluoroethane | $CF_3CHClF$ | 0.0005 |
| Chlorotrifluoroethane | $CF_3CH_2Cl$ | 0.0041 |

The gas, after the removal of the acid content, was collected under cooling using a cylinder container and purified by distillation to remove low boiling fractions and high boiling fractions by a known method. The composition obtained after the purification was analyzed by gas chromatography and found to have the composition shown in Table 14.

TABLE 14

| Name of Compound | Chemical Formula | Composition (vol %) |
|---|---|---|
| 2H-Heptafluoropropane | $CF_3CHFCF_3$ | 99.9925 |
| Pentafluoroethane | $CF_3CHF_2$ | 0.0009 |
| Octafluoropropane | $CF_3CF_2CF_3$ | 0.0002 |
| Hexafluoropropene | $CF_3CF=CF_2$ | 0.0016 |
| Chloropentafluoroethane | $CF_3CClF_2$ | 0.0014 |
| Tetrafluoroethane | $CF_3CH_2F$ | 0.0025 |
| Dichlorodifluoromethane | $CCl_2F_2$ | 0.0009 |

From the results shown in Table 14, it was found that chlorine compounds contained as impurities in 2H-heptafluoropropane can be reduced to 0.01 vol % or less by distillation.

EXAMPLE 5

A reaction was performed by the same operation and under the same conditions as in Example 2 except for using the purified product of 2H-heptafluoropropane described in Example 4. The gas, after the removal of the acid content, was collected under cooling using a cylinder container and purified by distillation to remove low boiling fractions and high boiling fractions by a known method. The composition obtained was analyzed by gas chromatography and found to have the composition shown in Table 15.

TABLE 15

| Name of Compound | Chemical Formula | Composition (vol %) |
|---|---|---|
| Octafluoropropane | $CF_3CF_2CF_3$ | 99.9979 |
| Chloropentafluoroethane | $CF_3CClF_2$ | 0.0015 |
| Dichlorodifluoromethane | $CCl_2F_2$ | 0.0006 |

As is proved from the results shown in Table 15, octafluoropropane having a purity of 99.995 vol % or more can be obtained.

Industrial Applicability

As described in the foregoing pages, when the process of the present invention is used, high-purity octafluoropropane can be produced from hexafluoropropene which may contain chlorine-containing impurities, and the high-purity octafluoropropane produced by using the present invention can be used as an etching or cleaning gas in the process of manufacturing a semiconductor device.

What is claimed is:

1. A process for producing octafluoropropane, comprising:
    (1) a step of reacting hexafluoropropene with hydrogen fluoride in a gas phase at a temperature of approximately from 150 to 450° C. in the presence of a fluorination catalyst to obtain 2H-heptafluoropropane; and
    (2) a step of reacting 2H-heptafluoropropane obtained in step (1) with fluorine gas in a gas phase at a temperature of approximately from 250 to 500° C. in the absence of a catalyst to obtain octafluoropropane.

2. A process as claimed in claim 1, wherein the hexafluoropropene contains at least one compound selected from the group consisting of dichlorodifluoromethane, chlorodifluoromethane, chloropentafluoroethane, chlorotetrafluoroethane and chlorotrifluoroethylene.

3. A process as claimed in claim 1, wherein, in step (1), the fluorination catalyst is a bulk catalyst mainly comprising an oxide of chromium and is obtained by adding at least one member selected from the group consisting of indium, zinc and nickel.

4. A process as claimed in claim 1, wherein in the step (1), the molar ratio of hydrogen fluoride/hexafluoropropene is in the range from 0.8 to 3:1.

5. A process as claimed in claim 1, which further comprises a step of removing impurities contained in 2H-heptafluoropropane before step (2).

6. A process as claimed in claim 5, wherein the impurities are at least one compound selected from the group consisting of tetrafluoromethane, trifluoromethane, chlorotrifluoromethane, hexafluoroethane and pentafluoroethane.

7. A process as claimed in claims 5 or 6, wherein the step of removing impurities contained in 2H-heptafluoropropane is a distillation step.

8. A process as claimed in claim 1, wherein the 2H-heptafluoropropane has a chlorine compound content of 0.01 vol % or less.

9. A process as claimed in claim 1, wherein step (2) is performed in the presence of a diluting gas and the diluting gas is at least one gas selected from the group consisting of hydrogen fluoride, tetrafluoromethane, hexafluoroethane and octafluoropropane.

10. A process as claimed in claim 1, wherein, in step (2), the molar ratio of fluorine gas/2H-heptafluoropropane is in the range from 0.9 to 1.5:1.

11. A process as claimed in claim 1, wherein, in step (2), the concentration of 2H-heptafluoropropane at the reactor inlet is 8 mol % or less.

12. A process as claimed in claim 1, wherein at least a part of the outlet gas of step (2) is circulated and reused as a diluting gas in step (2).

13. A process as claimed in claim 1, which comprises a step of reacting at least a part of the outlet gas of step (2) with at least one hydrofluorocarbon to remove unreacted fluorine gas contained the outlet gas.

14. A process as claimed in claim 13, wherein the hydrofluorocarbon is selected from the group consisting of trifluorocarbon, tetrafluoroethane, pentafluoroethane and 2-heptafluoropropane.

15. A process as claimed in claim 1, wherein hydrogen fluoride contained in the outlet gas of step (2) is separated and the separated hydrogen fluoride is returned to step (1) and/or step (2).

16. A process as claimed in claim 1, wherein at least a part of octafluoropropane is separated from the gas after the separation of hydrogen fluoride, and the remaining gas is returned to step (1) and/or step (2).

* * * * *